(12) United States Patent
Siccardi et al.

(10) Patent No.: US 9,936,980 B2
(45) Date of Patent: Apr. 10, 2018

(54) DEVICE FOR FIXING SURGICAL IMPLANTS IN PLACE AND RELATIVE ASSEMBLY PROCEDURE WITH ANCHORING MEANS

(71) Applicant: MEDACTA INTERNATIONAL SA, Castel San Pietro (CH)

(72) Inventors: Francesco Siccardi, Sonvico (CH); Daniele Beretta, Maslianico (IT); Meinrad Fiechter, Lugano (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 0 days.

(21) Appl. No.: 15/302,192

(22) PCT Filed: Apr. 8, 2015

(86) PCT No.: PCT/IB2015/052540
§ 371 (c)(1),
(2) Date: Oct. 6, 2016

(87) PCT Pub. No.: WO2015/155702
PCT Pub. Date: Oct. 15, 2015

(65) Prior Publication Data
US 2017/0020576 A1 Jan. 26, 2017

(30) Foreign Application Priority Data
Apr. 10, 2014 (IT) .............................. MI2014A0674

(51) Int. Cl.
*A61B 17/70* (2006.01)
*A61B 17/56* (2006.01)
*A61B 17/68* (2006.01)

(52) U.S. Cl.
CPC ...... *A61B 17/7037* (2013.01); *A61B 17/7034* (2013.01); *A61B 2017/567* (2013.01); *A61B 2017/681* (2013.01)

(58) Field of Classification Search
CPC ............ A61B 17/7037; A61B 17/7034; A61B 17/7032; A61B 17/7038;
(Continued)

(56) References Cited

U.S. PATENT DOCUMENTS

| | | |
|---|---|---|
| 5,569,246 A | 10/1996 | Ojima et al. |
| 5,915,968 A | 6/1999 | Kirsch et al. |

(Continued)

FOREIGN PATENT DOCUMENTS

| | | |
|---|---|---|
| EP | 2638874 A2 | 9/2013 |
| FR | 2845268 A1 | 4/2004 |

(Continued)

*Primary Examiner* — Pedro Philogene
(74) *Attorney, Agent, or Firm* — Allen, Dyer, Doppelt + Gilchrist, P.A. Attorneys at Law

(57) ABSTRACT

A device is for fixing surgical implants in place. The device may include a central body having an axially hollow upper zone, and an axially hollow lower zone. The upper and lower zones may form a single body being open at the bottom and at the top. A central through cavity may extend inside the upper and lower zones. The upper zone may have two portions projecting axially from the upper zone, divided from each other by two through U-shaped slots and forming, in conjunction with part of the central cavity, a channel for housing a connection rod. The lower zone may include a slot for the lateral access to the central cavity of an anchoring device. The slot may be in a conformation such as to permit the lateral insertion of the anchoring device inside the central cavity.

16 Claims, 11 Drawing Sheets

(58) Field of Classification Search
CPC .... A61B 2017/00858; A61B 2017/567; A61B 2017/681; Y10T 29/49862
USPC .................... 606/246–279, 60, 300–331
See application file for complete search history.

(56) References Cited

U.S. PATENT DOCUMENTS

| | | | |
|---|---|---|---|
| 6,056,753 A | 5/2000 | Jackson | |
| 6,471,705 B1 | 10/2002 | Biedermann et al. | |
| 7,081,116 B1 | 7/2006 | Carly | |
| 7,125,426 B2 | 10/2006 | Moumene et al. | |
| 7,156,850 B2 | 1/2007 | Kim | |
| 7,211,086 B2 | 5/2007 | Biedermann et al. | |
| 7,276,069 B2 | 10/2007 | Biedermann et al. | |
| 7,294,128 B2 | 11/2007 | Alleyne et al. | |
| 7,766,945 B2 | 8/2010 | Nilsson et al. | |
| 7,785,354 B2 | 8/2010 | Biedermann et al. | |
| 8,167,913 B2 | 5/2012 | Albert et al. | |
| 2003/0045879 A1 | 3/2003 | Minfelde et al. | |
| 2003/0100904 A1 | 5/2003 | Biedermann | |
| 2004/0254579 A1 | 12/2004 | Buhren et al. | |
| 2005/0171542 A1 | 8/2005 | Biedermann et al. | |
| 2005/0273101 A1 | 12/2005 | Schumacher | |
| 2006/0195098 A1 | 8/2006 | Schumacher | |
| 2007/0055240 A1 | 3/2007 | Matthis et al. | |
| 2007/0265621 A1 | 11/2007 | Matthis et al. | |
| 2008/0015579 A1 | 1/2008 | Whipple | |
| 2008/0021455 A1* | 1/2008 | Chao | A61B 17/7034 606/250 |
| 2008/0119895 A1 | 5/2008 | Manceau | |
| 2008/0243185 A1 | 10/2008 | Felix et al. | |
| 2008/0312696 A1 | 12/2008 | Butters et al. | |
| 2010/0160965 A1 | 6/2010 | Viker | |
| 2010/0234902 A1 | 9/2010 | Biedermann et al. | |
| 2012/0303072 A1* | 11/2012 | Eisermann | A61B 17/7037 606/305 |
| 2013/0103097 A1* | 4/2013 | May | A61B 17/7032 606/305 |
| 2013/0110178 A1* | 5/2013 | Biedermann | A61B 17/7037 606/305 |
| 2015/0359568 A1* | 12/2015 | Rezach | A61B 17/7032 606/266 |

FOREIGN PATENT DOCUMENTS

| | | |
|---|---|---|
| FR | 2845269 A1 | 4/2004 |
| WO | 2005065413 A2 | 7/2005 |
| WO | 2012162551 A2 | 11/2012 |

* cited by examiner

SECTION XI-XI

DEVICE FOR FIXING SURGICAL IMPLANTS IN PLACE AND RELATIVE ASSEMBLY PROCEDURE WITH ANCHORING MEANS

RELATED APPLICATION

This application is based upon prior filed copending International Application No. PCT/IB2015/052540 filed Apr. 8, 2015, which claims priority to Italian Application No. MI2014A000674, filed Apr. 10, 2014, the entire subject matter of these applications is incorporated herein by reference in its entirety.

TECHNICAL FIELD

The present invention discloses a device for fixing surgical implants, and more particularly to an anchoring device and related methods.

BACKGROUND

Systems are known in the state of the art for fixing surgical implants, which have a polyaxial screw coupled with an overlying element, known in the state of the art as a tulip. The tulip has a substantially cup-shaped conformation and has an upper free end that is open and has lateral through U-shaped slots and a lower end, hollow inside, having a through-hole. The lower end houses, within it, the head of the polyaxial screw so that the connecting part between the head of the polyaxial screw and the stem of the polyaxial screw occupies the through-hole so that the stem of the polyaxial screw extends outside the lower end of the tulip. The head of the polyaxial screw is retained within the lower end of the tulip, free to rotate. Within the tulip, above the head of the polyaxial screw, a connection bar is inserted radially into the tulip and coming out of it through the U-shaped slots, adapted to connect various systems for fixing surgical implants to one another during the placement of the implants. Above the connection bar, by means of a threaded coupling, a set screw is coupled to the tulip, adapted to press against the connection bar in order to bring it into contact with the head of the polyaxial screw and transmit the pressure imposed by the set screw to it, so that the head of the polyaxial screw is blocked in the desired position and is not, therefore, able to rotate further with respect to the tulip.

The system for fixing surgical implants described above is usually provided for its placement already assembled, i.e. with the head of the polyaxial screw coupled to the tulip. The surgeon has the task of inserting the connection bar and proceeding with the definitive assembly through the set screw.

For coupling the tulip to the head of the polyaxial screw, therefore, the known technique envisions inserting the stem of the screw through the upper free end of the tulip itself and making the stem of the polyaxial screw pass through the central body of the tulip until it comes out of the hole provided in the lower end. In this way, the stem of the polyaxial screw protrudes for the whole of its length from the lower end of the tulip, while the head of the polyaxial screw, due to its larger dimensions with respect to its stem, remains retained within the tulip. To prevent the polyaxial screw coming out of the top of the tulip a blocking element is used that acts directly on the head of the screw to prevent its axial movement but that is able to allow its rotation.

SUMMARY

Generally speaking, a device is for fixing surgical implants in place. The device may include a central body having an axially hollow upper zone, and an axially hollow lower zone. The upper and lower zones may form a single body being open at the bottom and at the top. A central through cavity may extend inside the upper and lower zones. The upper zone may have two portions projecting axially from the upper zone, divided from each other by two through U-shaped slots and forming, in conjunction with part of the central cavity, a channel for housing a connection rod. The lower zone may include a slot for the lateral access to the central cavity of an anchoring device. The slot may be in a conformation such as to permit the lateral insertion of the anchoring device inside the central cavity by the relative translation of the central body and the anchoring device and the axial alignment of the central body and the anchoring device.

DETAILED DESCRIPTION

Figure 1:
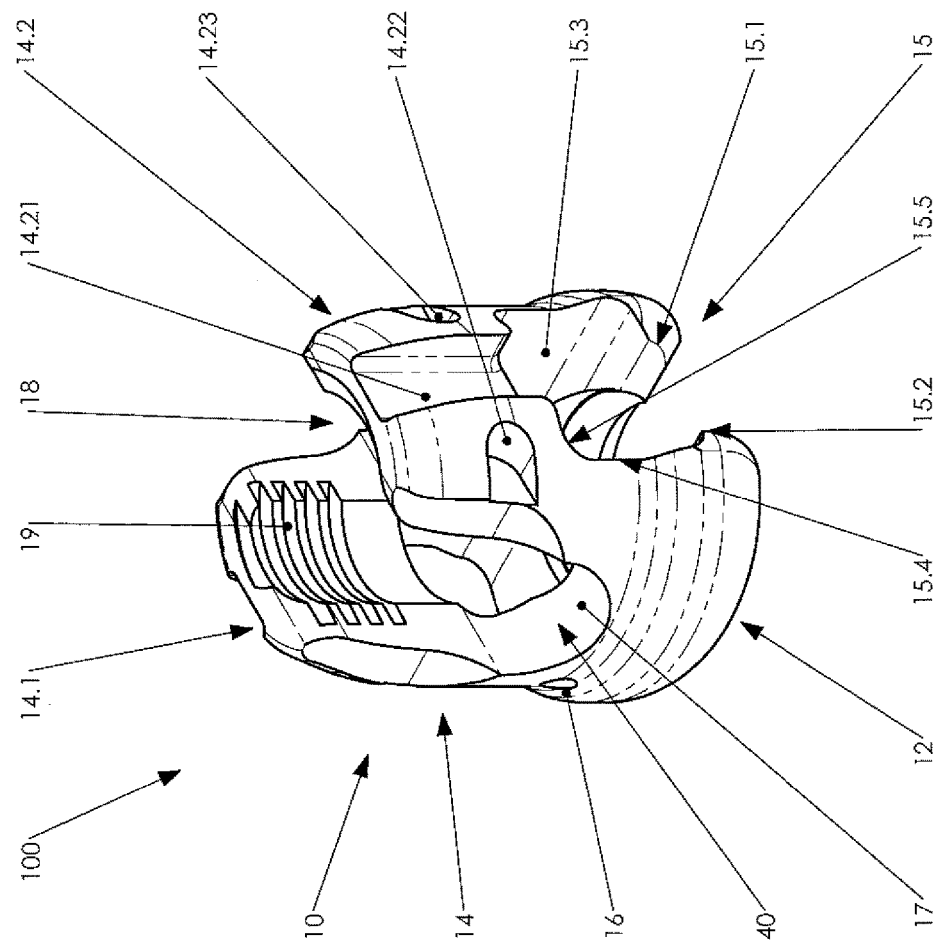
FIG. 1 is a perspective view of the device for fixing surgical implants according to the present invention.

As appears clearly from the above description, the need to make the stem of the polyaxial screw pass into the tulip in order to partially assemble the device for fixing surgical implants imposes limits on the minimum inner diameter of the tulip. In fact, if the tulip had a smaller inner diameter than the outer diameter of the threaded stem it would not be possible for the latter to cross it until it protrudes out of its lower end. Therefore, the minimum inner diameter possible for the tulip is the outer diameter of the stem of the screw coupled thereto. Hence, as the outer diameter of the screw increases, the size of the tulip increases as a result.

However, the diameter of the tulip cannot increase as preferred, since the device for fixing surgical implants is also used in minimally invasive surgery in which the dimensions of the access area to the patient's skeletal structure are minimal. To overcome this drawback a system has been disclosed for stabilizing a surgical implant envisaging the use of a fixing system with an upper connection element that can be likened to a tulip, to be coupled with a polyaxial screw. The system is the subject matter of document U.S. Pat. No. 8,167,913 to Albert et al., assigned to Altus Partners LLC.

This approach discloses a polyaxial screw having the head of the screw, integrally connected to a threaded stem through a connection area, known as the neck of the polyaxial screw, the head of the polyaxial screw comprising two parts: a first part integral with the neck and a second part detachably coupled to the first part through, for example, a force coupling. The head of the polyaxial screw is adapted to be coupled to an upper connection element which, due to its function and positioning in the device, can be likened to a tulip. The upper connection element has a substantially prolate spheroidal shape truncated at the top, axially hollow and with its vertex facing downwards. In its upper end, it has two projections adapted to receive and contain a connection bar between them. On the top of one of the two projections there is a threaded coupling area for the coupling of a set screw. The shape of the projection and the coupling area is such that, when the set screw is in the coupling configuration its end comes into contact with the connection bar pressing it downwards.

The vertex area of the upper connection element is hollow inside and comprises a through opening positioned partially on the bottom surface and partially on a side of the upper connection element. To assemble the polyaxial screw and the upper connection element the first part of the head of the screw, integral with the stem of the polyaxial screw, is inserted through the opening portion located on the side of the vertex area of the upper connection element, keeping the stem of the screw in a perpendicular position to the central axis of the upper connection element. When the first part of the head is completely inserted into the axial cavity of the upper connection element, the coupling is made between the first and the second part of the screw head keeping the stem of the screw in a perpendicular position to the central axis of the upper connection element and inserting the latter from above, through the upper connection element.

In this way, thanks to the coupling described above, the head of the polyaxial screw assumes a spherical shape with dimensions such as not to be able to come out of the seating in which it is inserted within the upper connection element, hence making the coupling between the polyaxial screw and the upper connection element. Above the spherical head of the polyaxial screw the seating in which the connection bar is housed is present. The connection bar has a circular section and is housed in its seating, provided in the upper connection element, so as to strike against the spherical head of the polyaxial screw. Hence a set screw is coupled to the upper connection element so as to press tangentially against the connection bar and impose a compression on it in the axial direction with respect to the upper connection element. The pressure forces the connection bar to press in turn against the spherical head of the polyaxial screw blocking it in the desired position.

However, what is disclosed by U.S. Pat. No. 8,167,913 also has some drawbacks. In fact, the assembled configuration of the head of the spherical screw is obtained by inserting the second part of the head of the spherical screw through the axial cavity of the upper connection element, until it reaches the seating in which the first part of the spherical head of the polyaxial screw can be found and therefore proceed with the coupling. This procedure, as can be clearly understood by the person skilled in the art, requires the upper connection element to have an axial cavity of sufficient dimensions so that it is possible to operate within it and insert the second part of the spherical head of the polyaxial screw therein. Therefore, it will not be possible to reduce the dimensions of the upper connection element below a threshold value that is such as to guarantee the passage of the second part of the head of the spherical screw.

It is also known to a person skilled in the art that a coupling between two mechanical parts cannot allow a perfect geometric shape to be obtained as provided by a body made of a single part unless particularly expensive processing is performed. Therefore, the production of the head of the polyaxial screw in two parts, as disclosed by U.S. Pat. No. 8,167,913, can cause a limitation of the possibilities for relative movement between the upper connection element and the head of the screw due to an imperfect coupling between the two parts forming the head of the screw.

The coupling between the first and the second part of the head of the screw imposes the provision of a seating for the coupling between the two that is such as to guarantee perfect fixing between the two parts in order to obtain a reliable assembly. This characteristic imposes dimensions of the screw head such as to allow the creation of the coupling seating however keeping the necessary space for the engagement seating provided for the coupling with a known instrument, for example a screwdriver, between the head of the polyaxial screw and the instrument.

Furthermore, the actual shape of the spherical head of the polyaxial screw, for the successful coupling of the two parts that comprise it, imposes a fairly reduced contact surface between the spherical head of the polyaxial screw and the connection bar, which can be likened to a punctiform contact. This means that the pressure imposed by the set screw on the connection bar and by it on the spherical head of the polyaxial screw is transmitted by almost punctiform contact. This type of contact can lead to relative movements between the parts with the consequent unstable fixing of the implant and wear of the elements involved.

Not only, in fact, the conformation envisaged in document U.S. Pat. No. 8,167,913 does not make it possible to temporarily block the polyaxial screw in its relative movement with respect to the upper connection element. The blocking is important in order to achieve the correct placement of the surgical implant and to simplify the operations for the surgeon.

Furthermore, the method for the assembly of the device according to U.S. Pat. No. 8,167,913 includes complex operations that require time and dedicated equipment, especially when the characteristic dimensions of the spherical head of the polyaxial screw and, consequently, the upper connection element, are reduced. Finally, the superficial characteristics required for the correct assembly of the device according to U.S. Pat. No. 8,167,913 impose expensive and complex processing operations on the material, just as the assembly operations for the aforementioned device are long and complex.

Starting from the notion of these disadvantages, the present invention intends to provide a remedy for them.

An object of the present invention is to provide a device for fixing surgical implants that can minimize the dimensions of the implant. Another object of the present invention is to provide a device for fixing surgical implants that provides the possibility to be coupled to anchoring means having any characteristic dimensions.

Another object of the present invention is to provide a device as specified that can provide a simplified, quick and cheap assembly procedure. Another object of the present invention is to provide a device for fixing surgical implants that provides stable fixing of the implant preventing the incorrect positioning of the elements involved in the implant and/or relative movements between them.

It is also an object of the present invention to provide a fixing device as specified which provides the possibility to temporarily block the relative movement between an anchoring device and the fixing device, for the purpose of the correct positioning of the surgical implant. Finally, an object of the present invention is to provide a device for fixing surgical implants that is easy to use, has reduced dimensions and costs and is reliable to use.

In the drawing, 100 indicates the device for fixing surgical implants as a whole. It substantially comprises a central body 10 having a truncated cone shape, with a through cylindrical axial cavity and having two zones: an upper zone 14 and a lower zone 12. In the upper zone 14 of the central body 10, there are two through U-shaped slots 17 and 18 occupying the whole axial extension of the upper zone 14 of the central body 10. The slots 17 and 18 divide the upper zone 14 of the central body 10 into two distinct portions 14.1 and 14.2.

The two portions 14.1 and 14.2 have a circular crown sector section, are symmetrical to one another, arranged facing one another and each comprises an upper threaded free end with a female screw thread 19 and a lower end forming a single body with the lower zone 12, thus defining an upper axial cavity. At the lower ends of the portions 14.1 and 14.2 a channel 40 is identified, having a transversal axis with respect to the central axis of the central body 10, formed by the saddle-shaped end part of the U-shaped slots 17 and 18, and passing transversally through the upper axial cavity comprised between the two portions 14.1 and 14.2.

The lower zone 12 of the central body 10 has a toroidal shape, is axially hollow and has an external surface tapered towards the end part of the upper zone 14 of the central body 10 with which it forms a single body. Within the lower zone 12 there is a lower axial cavity, substantially cylindrically shaped, with upper 12.6 and lower 12.5 apertures. It should be noted that, in the area proximal to the lower aperture 12.5 there is a lip 12.2 projecting towards the inside of the lower axial cavity.

The lower axial cavity is coaxial with the upper axial cavity comprised between the two portions 14.1 and 14.2 and communicating therewith through the upper aperture 12.6. This conformation makes it possible to identify a central cavity meaning the sum of the lower and upper axial cavities and configures it as having an upper aperture between the two portions 14.1 and 14.2 and lower aperture coinciding with the lower aperture 12.5 of the lower axial cavity.

On one side of the lower zone 12 there is a lying-down C-shaped through slot 15. The lying-down C-shaped slot 15 mainly has two short sides 15.3 and 15.4 extending in the axial direction with respect to the central body 10 and a longer side 15.5 extending in the perpendicular direction to the two sides 15.3 and 15.4.

As can be seen in FIG. 1, at the opposite end of the sides 15.3 and 15.4 with respect to the long side 15.5 there are two protuberances 15.1 and 15.2. The lying-down C-shaped slot 15 also extends for the entire axial extension of the lower zone 12 and occupies part of the axial extension of the upper zone 14. Therefore, the perimeter of the lower aperture 12.5 of the lower axial cavity is interrupted by the lying-down C-shaped slot 15 and the lower axial cavity is open both laterally and at the bottom. In axial opposition to the C-shaped slot 15 there is a further aperture 31. The aperture 31 extends for a substantial part of the axial extension of the lower zone 12 and for part of the upper zone 14 and has an upper edge 31.1 and a lower edge 31.2. On one side 31.4 of the aperture 31 there is a through-hole 16. On the side 31.3 of the aperture 31, opposite the side 31.4 there is a seating 31.5.

Figure 2:
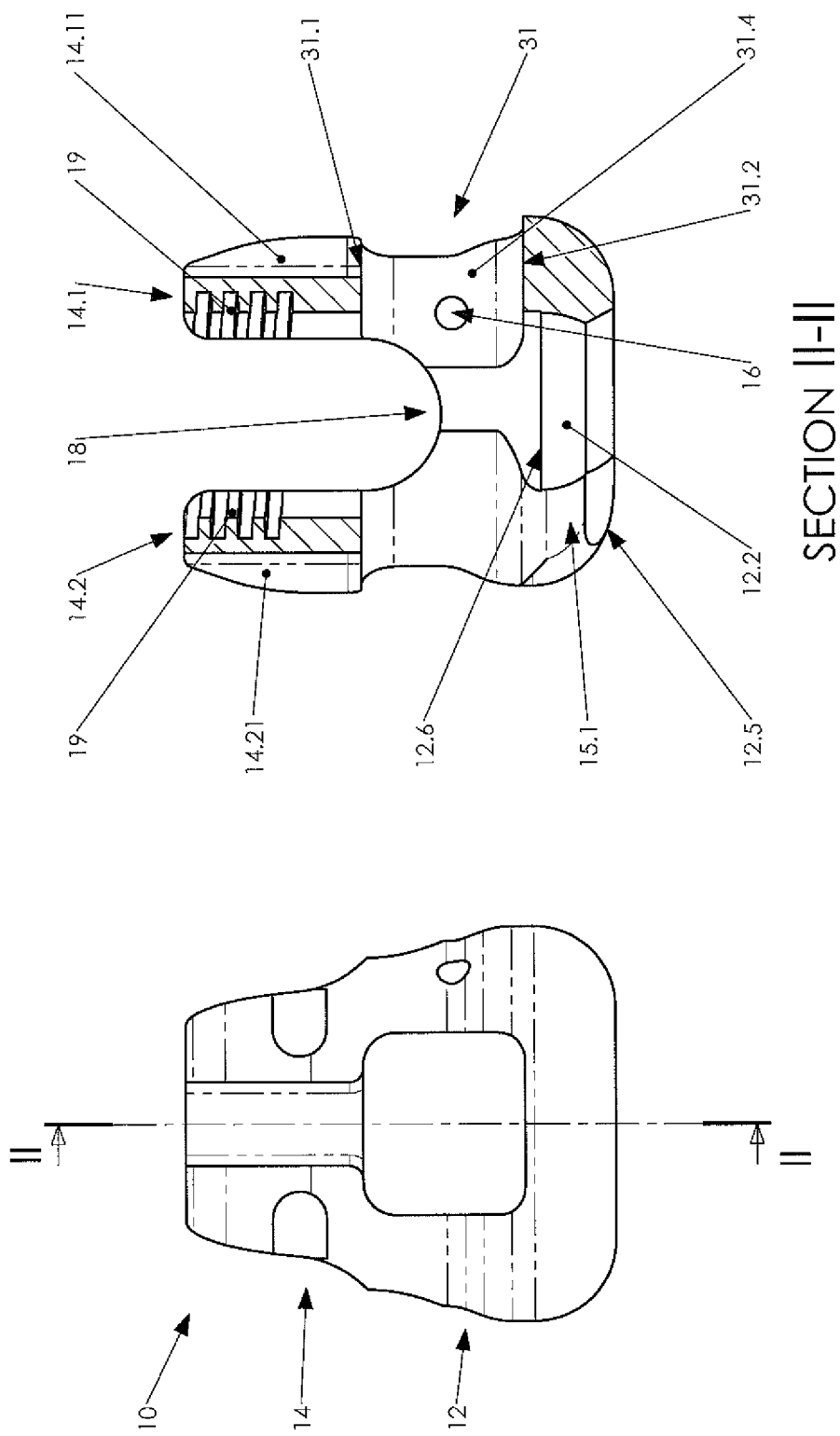
FIG. 2 is an orthogonal projection of the fixing device according to FIG. 1 and respective section according to line II-II in FIG. 1.
Figure 3:
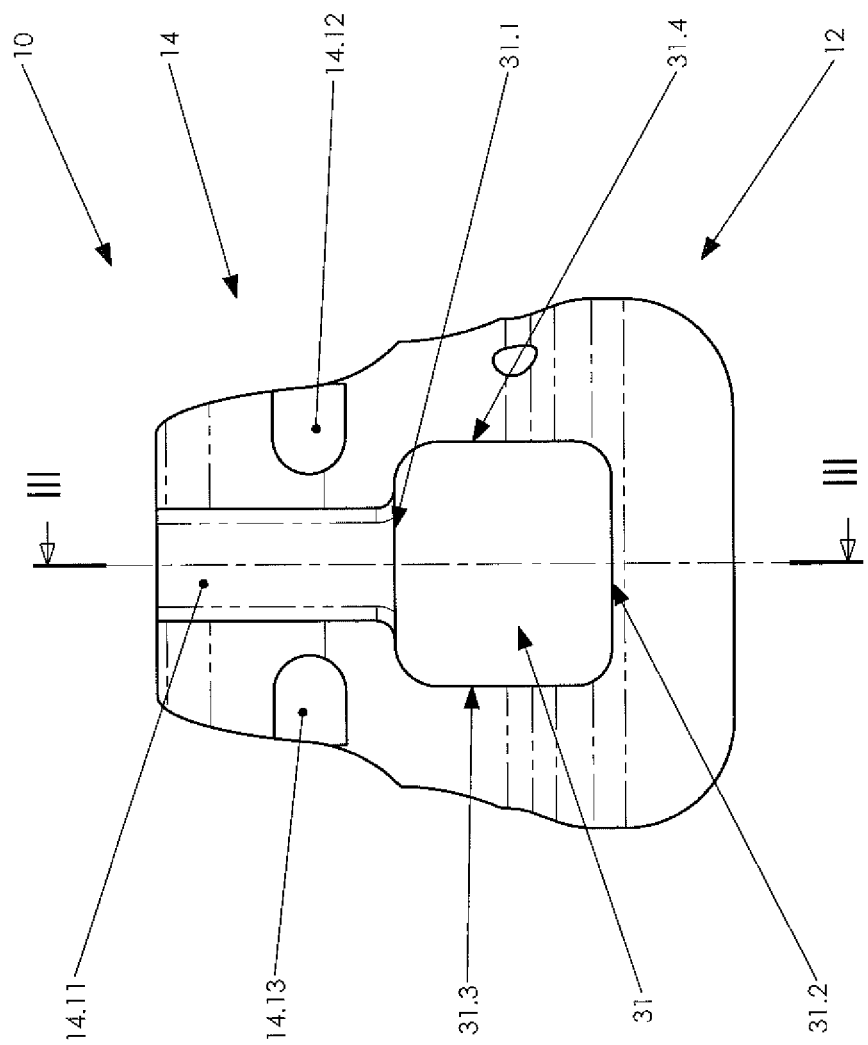
FIG. 3 is a rear view of the device for fixing surgical implants.
Figure 4:
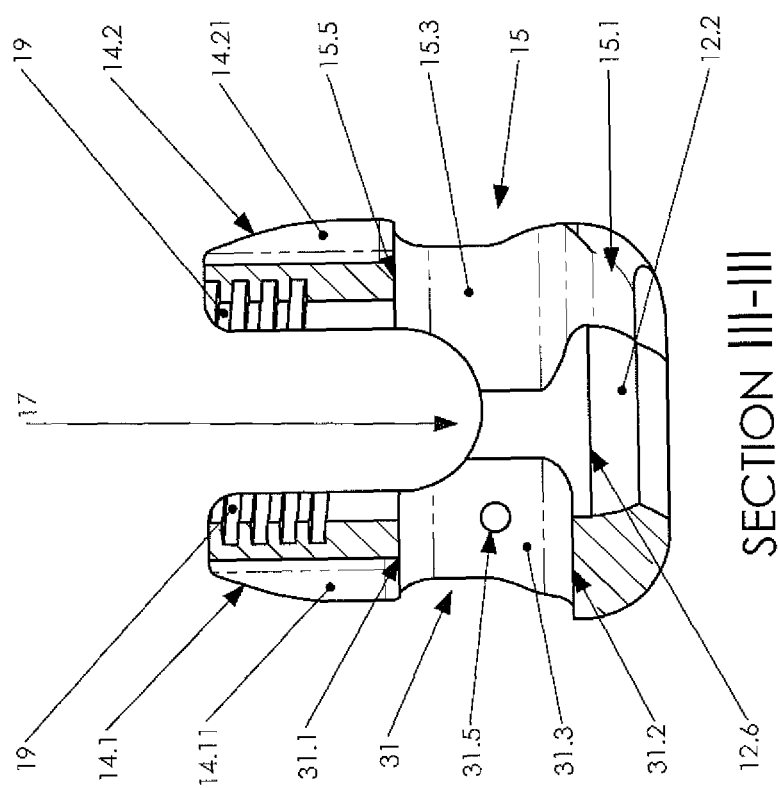
FIG. 4 is a sectional view according to line in FIG. 3.

As can be seen mainly from FIGS. 1.2 and 3 the upper zone 14 of the central body 10 has a plane of symmetry that passes through the central axis of the central body 10 and through the central axis of the channel 40, while the lower zone 12 of the central body 10 has a plane of symmetry passing through the central axis of the central body 10 and forming a right angle with the plane of symmetry of the upper zone 14. It also appears clearly from the image in FIG. 2 how the plane of symmetry of the lower zone 12 is also the plane of symmetry for the upper zone 14, but not vice versa. On the outer surface of portions 14.1 and 14.2 coupling elements can be identified, such as notches 14.12, 14.13, 14.22, 14.23 and grooves 14.11 and 14.21 for the coupling of the central body 10 with necessary known tools, for example screwdrivers.

Procedure

The device for fixing surgical implants is made to be coupled with known anchoring devices 20, for example a polyaxial screw. With reference to FIGS. 5 to 11, the polyaxial screw 20 comprises a head 21, a threaded stem 22 and a connection portion between the head 21 and the threaded stem 22, known as the neck 23 of the polyaxial screw 20. On the top of the head 21 of the polyaxial screw 20 a coupling area is provided adapted to house, within it, a known instrument, for example a screwdriver, able to control the polyaxial screw 20 for the coupling between the threaded stem 22 of the polyaxial screw 20 and the patient's bone structure.

Figure 5:
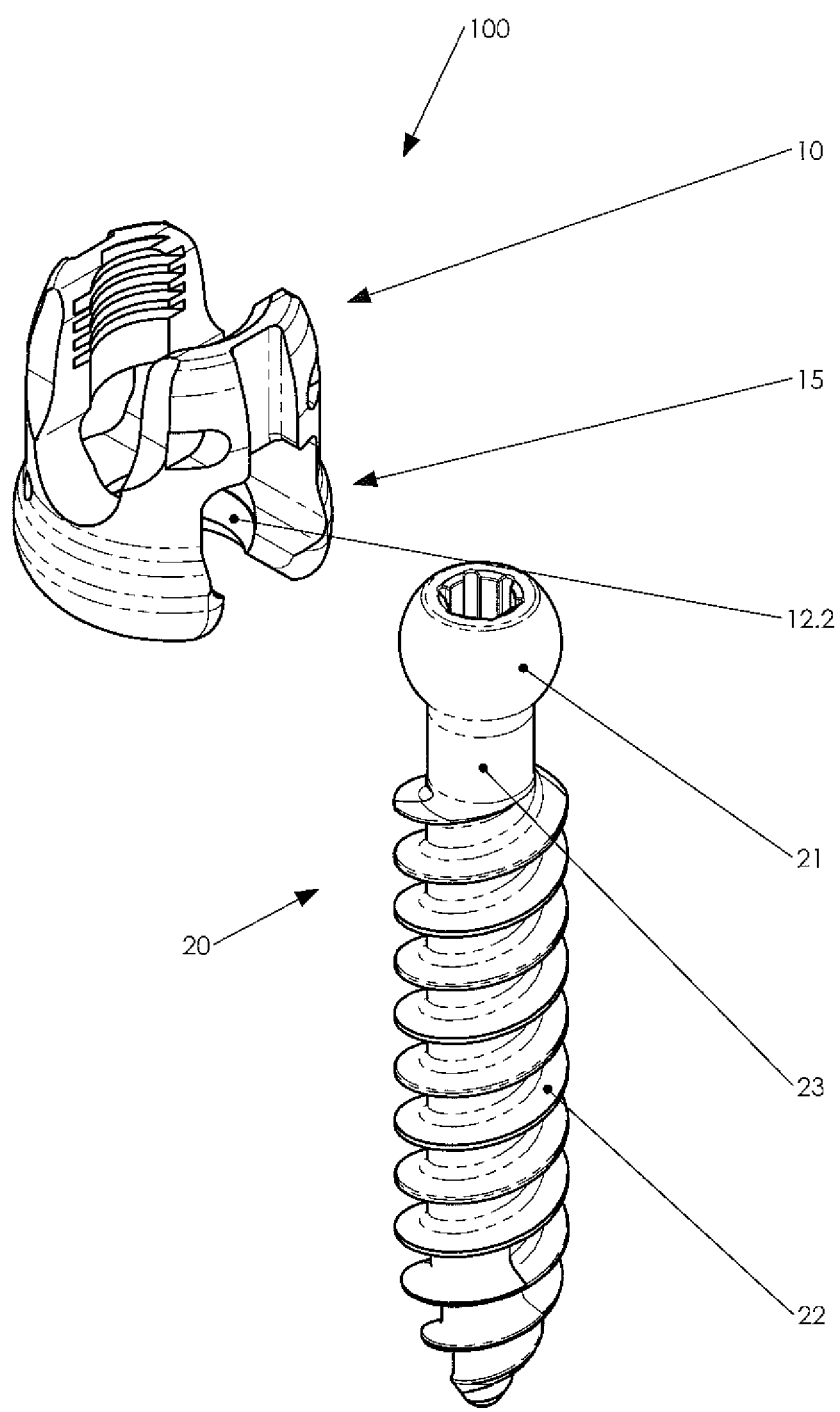
FIG. 5 is a side elevation view of the device according to the present invention in combination with a polyaxial screw during a first step of the coupling procedure according to the present invention.
Figure 6:
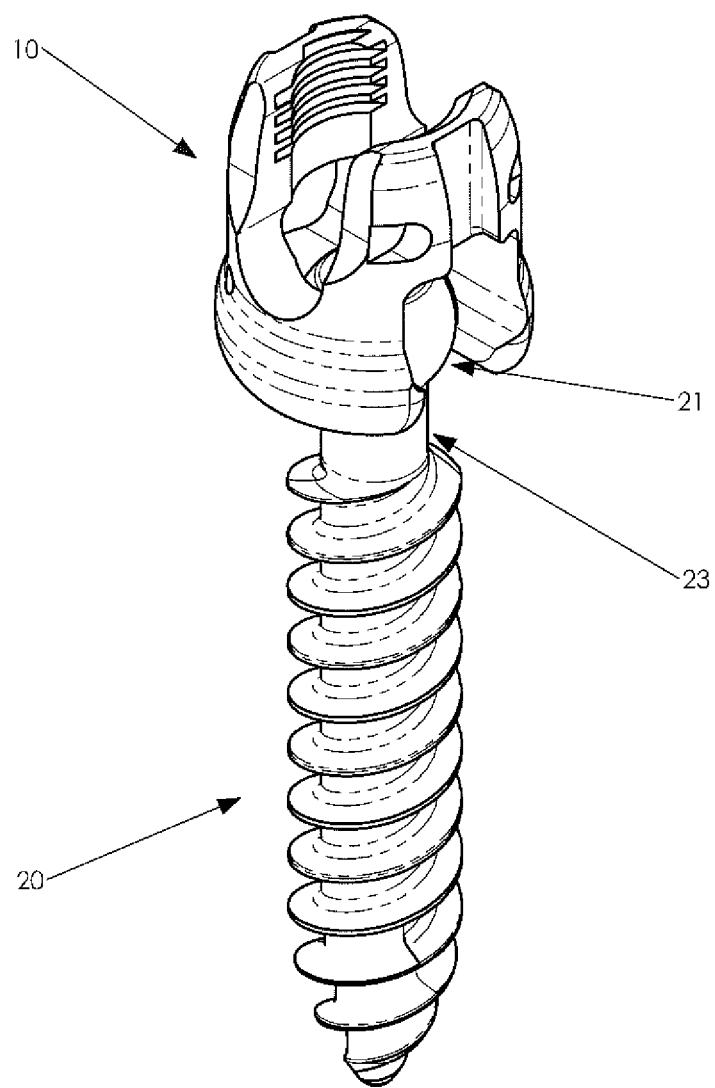
FIG. 6 is a side elevation view of the device for fixing a surgical implant in coupling with the polyaxial screw during a second step of the coupling procedure according to the present invention.
Figure 7:
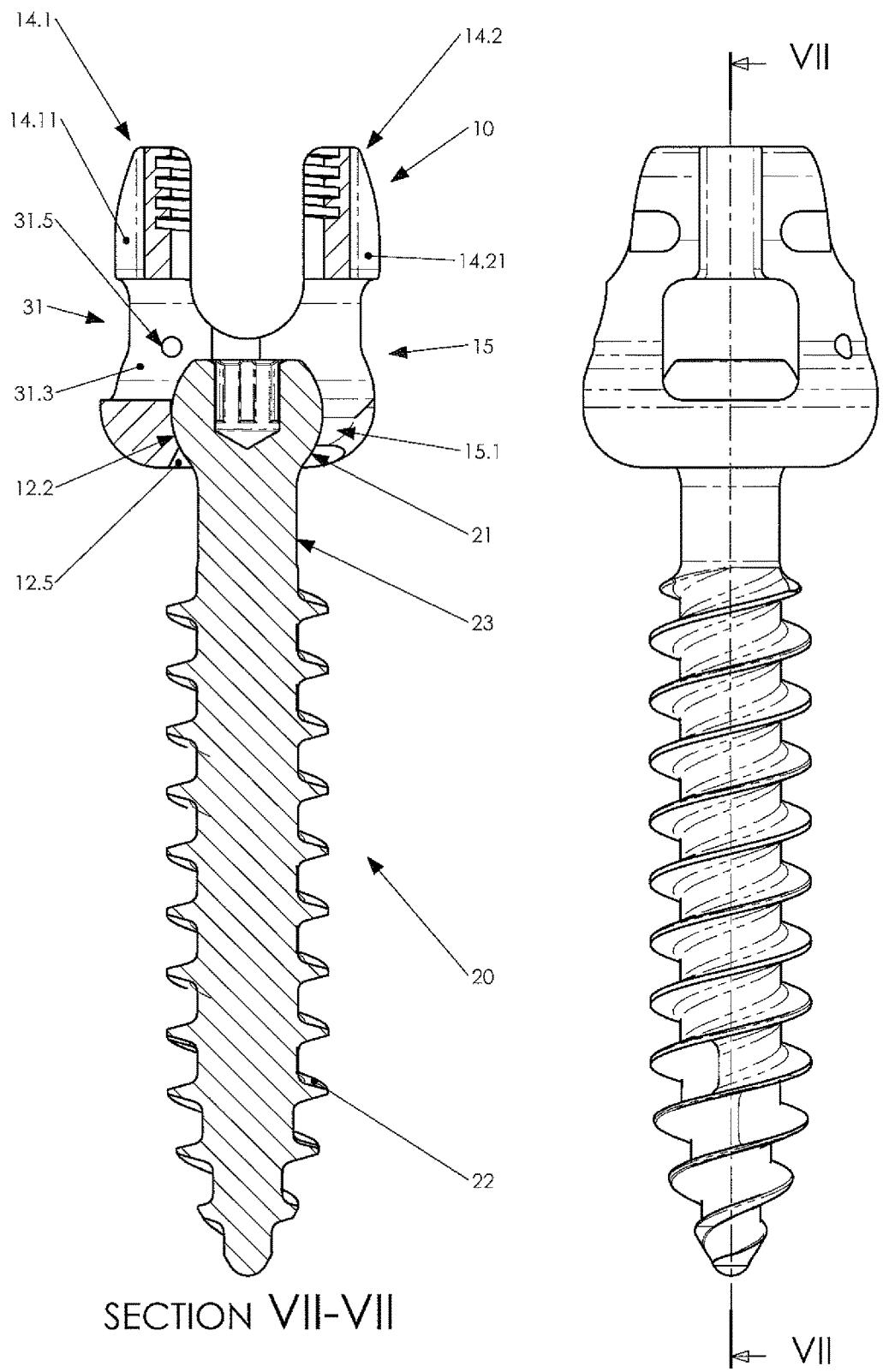
FIG. 7 is an orthogonal projection view of the device according to the present invention and respective sectional view according to line VII-VII in FIG. 6.

To proceed with the coupling of the device 100 for fixing surgical implants according to the present invention with an anchoring device 20, for example a polyaxial screw as illustrated in the exemplificative drawing, the central body 10 is positioned with the lying-down C-shaped slot 15 facing the head of the screw, as illustrated in FIG. 5. The shape of the slot 15 is such as to reproduce, slightly larger, the axial section of the head 21 of the polyaxial screw 20 and its neck 23.

Thanks to this conformation it is possible to make the head 21 of the polyaxial screw 20 and the neck 23 pass into the lying-down C-shaped slot 15 until the head 21 of the polyaxial screw 20 is brought into the lower axial cavity where it rests on the lip 12.2 present in the lower axial cavity. Note that the dimensions of the slot 15, the head 21 of the polyaxial screw 20 and the relative neck 23 are such that the passage of the head 21 and the neck 23 through the lying-down C-shaped slot 15 is only possible when the central axis of the central body 10 and the central axis of the polyaxial screw 20 are parallel. This characteristic prevents the head 21 of the polyaxial screw 20 accidentally coming out of the central body 10 through the slot 15 (FIG. 6) during the steps of this procedure.

Once the step of inserting the head 21 of the polyaxial screw 20 into the central body 10 has been completed, the head 21 is withheld at the bottom within the lower axial cavity by the lip 12.2 on which it rests (FIG. 7), while the neck 23 extends through the aperture 12.5 of the lower axial cavity and the stem 22 of the polyaxial screw 20 projects out of the central body 10. In this step of the procedure the head 21 of the polyaxial screw 20 is partially free to move, translating and rotating within the lower axial cavity.

Figure 8:
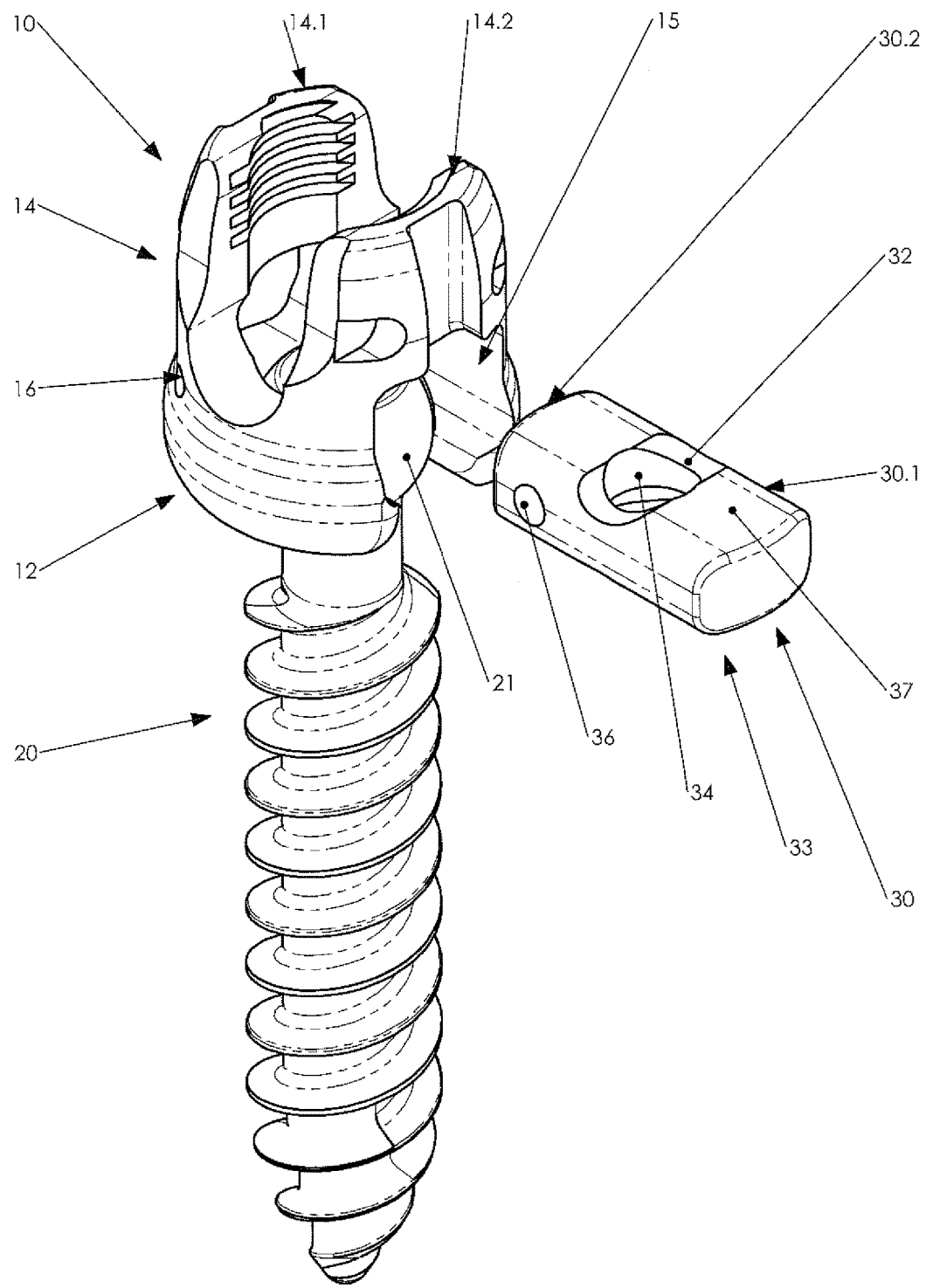
FIG. 8 is a side elevation view of the device for fixing a surgical implant in coupling with the polyaxial screw during a third step of the coupling procedure according to the present invention.
Figure 9:
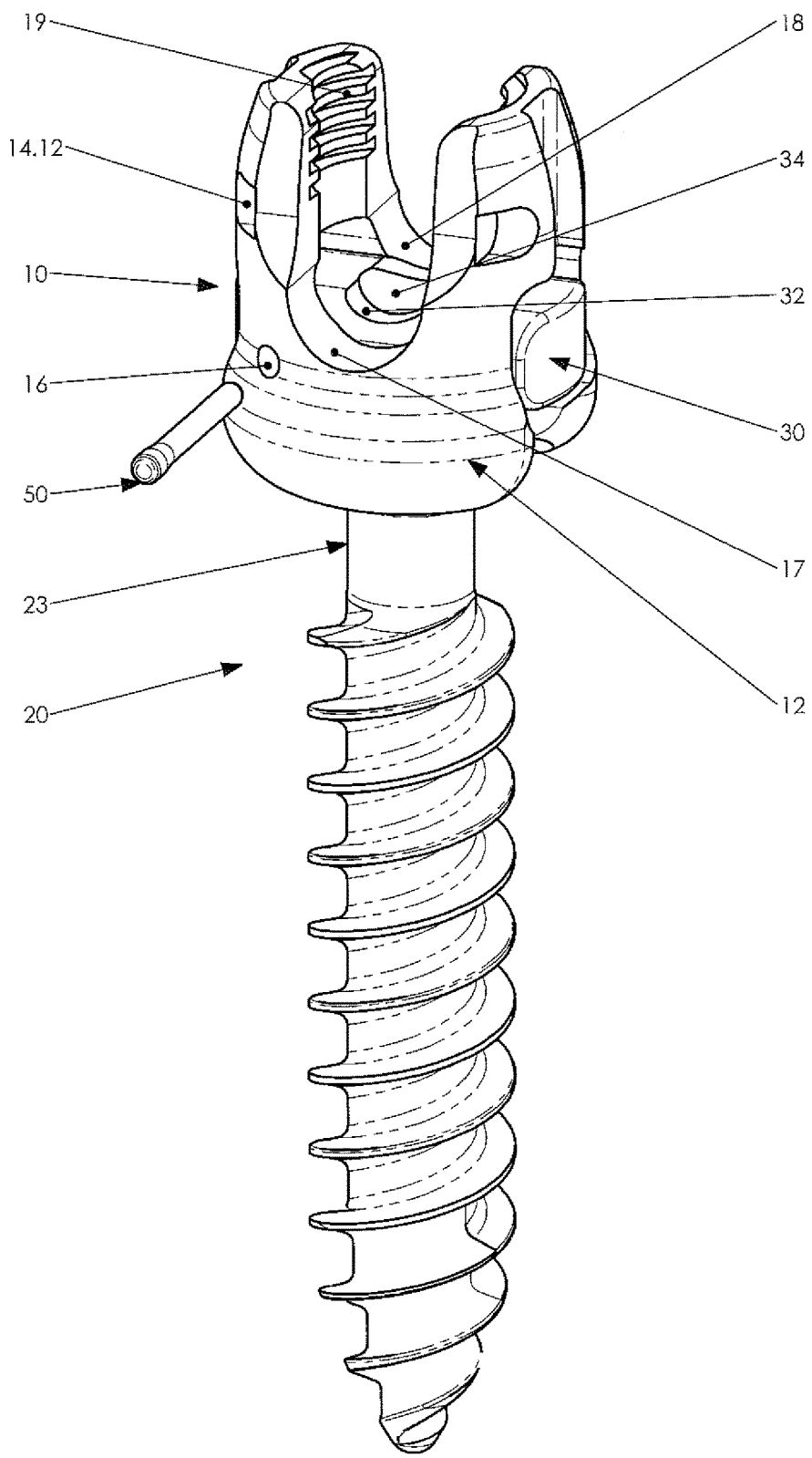
FIG. 9 is a side elevation view of the device for fixing a surgical implant in coupling with the polyaxial screw during a fourth step of the coupling procedure according to the present invention.
Figure 10:
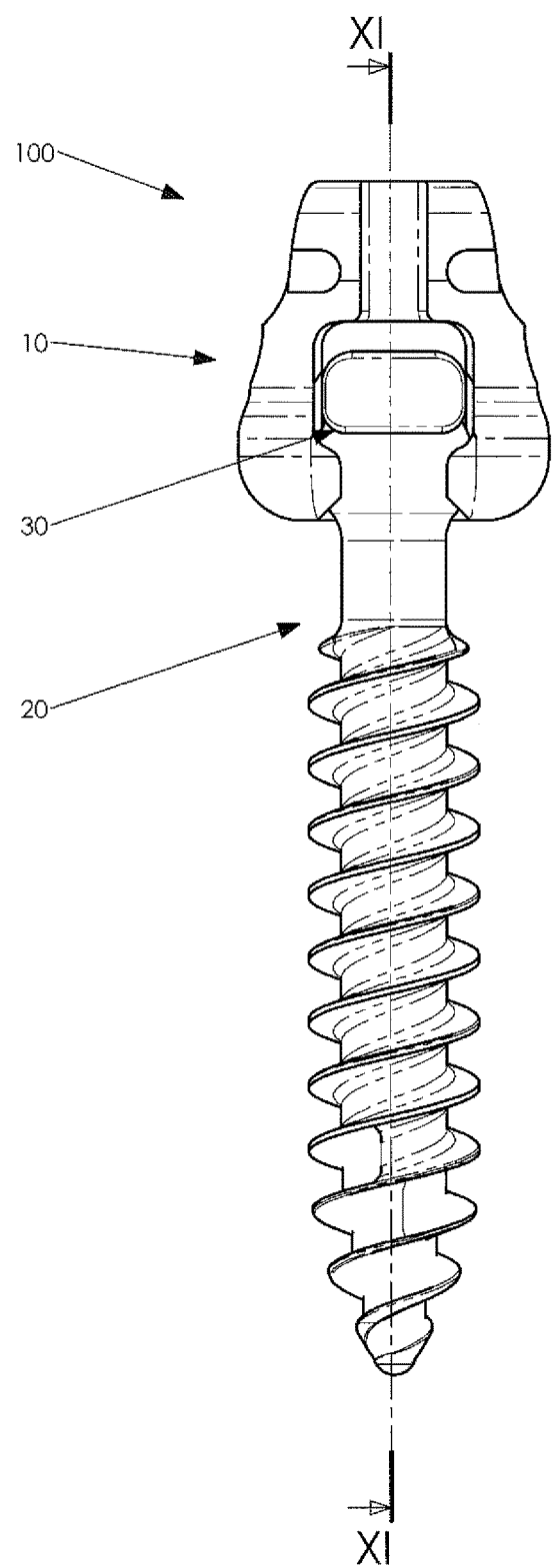
FIG. 10 is an orthogonal projection view of the device for fixing surgical implants at the end of the coupling procedure with the polyaxial screw according to the present invention.
Figure 11:
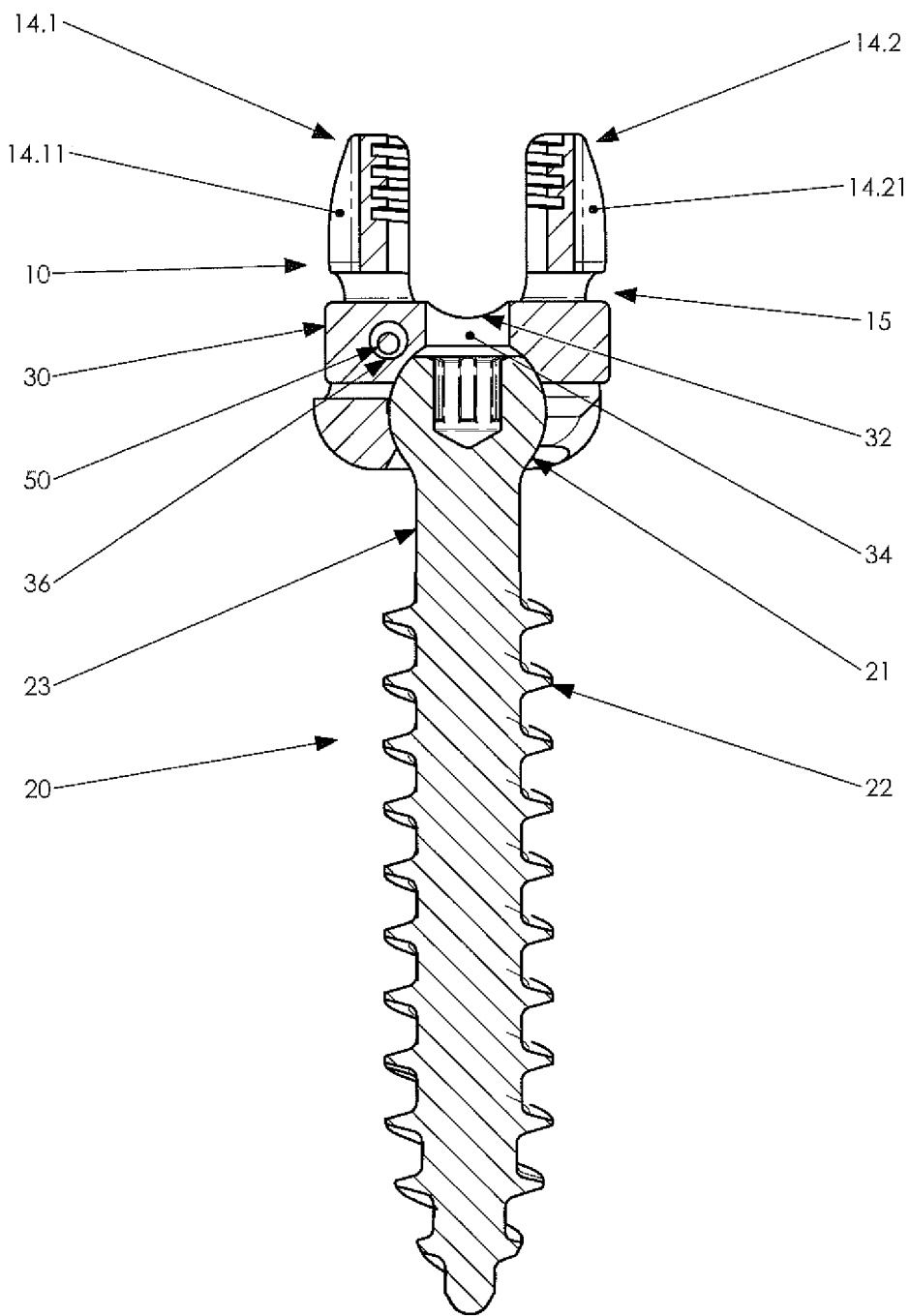
FIG. 11 is a sectional view according to line XI-XI in FIG. 10.

At this point, as illustrated in FIG. 8, an insert 30 is inserted through the slot 15. The insert 30 has a substantially parallelepiped shape with rounded corners and has a long side 30.1 defining the length of the insert 30 and a short side 30.2 defining the width of the insert 30. The upper face 37 of the insert 30 has a saddle-shaped, concave housing zone 32 transversal to the long side 30.1 and extending along the whole width of the insert 30. On the lower face 33 of the insert 30, there is a retaining area (not illustrated) adapted to house the top of the head 21 of the polyaxial screw 20. Furthermore, the central part of the insert 30 has a central through-hole 34. Near one of its sides 30.2, extending along the whole width of the insert 30, there is a through-hole 36.

The insert 30 is inserted, through the slot 15, in the top of the lower axial cavity, so as to rest on the head 21 of the polyaxial screw 20 and be in contact with it. In fact, the head 21 of the polyaxial screw 20 is housed within the retaining area (not illustrated) present in the lower face 33 of the insert 30. The central through-hole 34 also allows access to the coupling area provided on the top of the head 21 of the polyaxial screw 20.

The insertion of the insert 30 is correctly completed when the hole 36 is in an aligned position with the hole 16 provided in the side 31.4 of the aperture 31 on one side and with the seating 31.5 provided in the side 31.3 of the aperture 31 on the other. Furthermore, in this configuration, the housing zone 32 is positioned so as to act as a bottom wall of the channel 40.

At this point a blocking element, for example a connection pin 50, is inserted in the seating 31.5 of the side 31.3 of the aperture 31 through the hole 16 of the side 31.4 of the aperture 31, the hole 36 of the insert 30. The insertion of the pin takes place through interference, hence making the pin 50 integral with the structure and constraining the insert 30 in the desired position. The axial dimensions of the pin 30 are such that when it is inserted in the seating 31.5 it extends fully occupying the axial extension of the hole 36 of the insert 30 and almost entirely the hole 16 provided in the side 31.4 of the aperture 31.

Furthermore, once the insertion is correctly completed, the insert 30 projects above the side 31.2 of the aperture 31 on one side and the protuberances 15.1 and 15.2 of the lying-down C-shaped slot 15. In this way, through the grooves 14.21 and 14.11 it is possible to control the insert 30 in compression, potentially through a dedicated instrument, pressing against the head 21 of the polyaxial screw 20 and temporarily locking the position of the stem 22 of the screw 20.

Hence it is possible to proceed with the necessary operations and then remove the pressure imposed on the insert to unlock the relative movement between the central body 10 and the polyaxial screw 20. At the end of the procedure described above the device 100 for fixing surgical implants is connected not detachably with an anchoring device, for example a polyaxial screw 20. The polyaxial screw 20 is free to vary its inclination with respect to the fixing device 10.

As appears from the above, the assembly procedure of the device 100 for fixing surgical implants with an anchoring device, for example a polyaxial screw 20, comprises the following steps: positioning the central body 10 and the polyaxial screw 20 so that the central axis of the central body 10 and the central axis of the polyaxial screw 20 are substantially parallel; inserting the head 21 of the polyaxial screw 20, through a lying-down C-shaped slot 15, within a lower axial cavity provided within the lower zone 12 of the central body 10; inserting an insert 30 through the lying-down C-shaped slot 15 in a position overlooking the head 21 of the polyaxial screw 20, the insert being conformed so as to provide a retaining area for the head 21 of the polyaxial screw 20 on one side and to provide a saddle-shaped housing zone 32 for a connection bar in cooperation with the end part of the two U-shaped slots 17 and 18 on the other; and fixing the insert 30 to the central body 10 through a blocking means, for example a pin 50, inserted in the seating 31.5 and blocked by interference with respect to the central body 10 through the hole 16.

As appears clearly from the above description the present invention advantageously reaches the objects described above. Naturally numerous variants can be made to what is described and illustrated merely by way of non-limiting example, without for this reason departing from the protective scope of the present invention and therefore from the domain of the present industrial patent.

The invention claimed is:

1. A fixation device comprising:
 a receiving body having
  an upper zone having an open upper end, and
  a lower zone being integral with said upper zone to define, a single body, said lower zone having an open lower end opposite the open upper end,
  said upper and lower zones defining a central through cavity extending longitudinally,
 said upper zone comprising first and second arms extending longitudinally upward and defining a U-shaped slot therebetween for receiving
 in conjunction with a part of the central through cavity a connection rod, said lower zone defining a slot for lateral access to said central through cavity for an anchoring device;
 said slot configured to permit a lateral insertion of said anchoring device inside said central through cavity; and
 an insert configured to limit movement between the anchoring device and said receiving body, said insert having an upper face and a lower face opposite said lower face, said lower face defining a retaining area configured to receive an upper portion of a head of the anchoring device.

2. The fixation device according to claim 1 wherein each arm includes a respective groove configured to provide access to a surface of the insert.

3. The fixation device according to claim 1 further comprising a blocking device configured to keep the insert in position inside the central through cavity.

4. The fixation device according to claim 1 wherein the upper face of the insert defines a lateral recess configured to receive a connection rod.

5. The fixation device according to claim 1 wherein the insert defines a through passageway between the upper and lower faces and configured to provide access to the anchoring device.

6. The fixation device according to claim 1 wherein the anchoring device is temporarily blocked in position by pressure on the insert.

7. The fixation device according to claim 3 wherein said insert has opposing sides extending between said lower and upper faces; and wherein said insert defines adjacent one of said opposing sides a through hole configured to house said blocking device, said through hole extending along an entire whole width of said insert.

8. A method for assembling a fixation device, the method comprising:
  axially positioning a receiving body and an anchoring device in parallel;
  inserting at least an upper end of the anchoring device through a slot, inside a central through cavity of the receiving body by translation;
  inserting laterally inside said central through cavity an insert through the slot; and
  attaching the insert to the receiving body by a blocking motion.

9. A fixation device comprising:
  a receiving body having
    an upper zone having an open upper end, and
    a lower zone being integral with said upper zone to define a single body, said lower zone having an open lower end opposite the open upper end,
    said upper and lower zones defining a central through cavity extending longitudinally,
  said upper zone comprising first and second arms extending longitudinally upward and defining a U-shaped slot therebetween for receiving in conjunction with a part of the central through cavity a connection rod, said lower zone defining a slot for lateral access to said central through cavity for an anchoring device;
  said slot configured to permit a lateral insertion of said anchoring device inside said central through cavity;
  said lower zone of said receiving body comprising a lip inwardly projecting towards a lower part of the central through cavity to retain the anchoring device from below.

10. A fixation device comprising:
  a receiving body having
    an upper zone having an open upper end, and
    a lower zone being integral with said upper zone to define a single body, said lower zone having an open lower end opposite the open upper end,
    said upper and lower zones defining a central through cavity extending longitudinally,
  said upper zone comprising first and second arms extending longitudinally upward and defining a U-shaped slot therebetween for receiving in conjunction with a part of the central through cavity a connection rod, said lower zone defining a slot for lateral access to said central through cavity for an anchoring device;
  said slot configured to permit a lateral insertion of said anchoring device inside said central through cavity;
  said lower zone of said receiving body comprising a lip inwardly projecting towards a lower part of the central through cavity to retain the anchoring device from below; and
  an insert configured to limit movement between the anchoring device and said receiving body, said insert being inserted laterally into the slot.

11. The fixation device according to claim 10 wherein each arm includes a respective groove configured to provide access to a surface of the insert.

12. The fixation device according to claim 10 further comprising a blocking device configured to keep the insert in position inside the central through cavity.

13. The fixation device according to claim 12 wherein said insert has opposing sides extending between said lower and upper faces; and wherein said insert defines adjacent one of said opposing sides a through hole configured to house said blocking device, said through hole extending along an entire whole width of said insert.

14. The fixation device according to claim 10 wherein an upper face of the insert defines a lateral recess configured to receive a connection rod.

15. The fixation device according to claim 10 wherein the insert defines a through passageway between the upper and lower faces and configured to provide access to the anchoring device.

16. The fixation device according to claim 10 wherein the anchoring device is temporarily blocked in position by pressure on the insert.

* * * * *